United States Patent

Tarui et al.

[11] Patent Number: 6,119,508
[45] Date of Patent: Sep. 19, 2000

[54] MEASURING EQUIPMENT FOR ISOLATING A PLURALITY OF PROBES CONTACTING A SAMPLE

[75] Inventors: Yoshihiro Tarui; Takeshi Mori, both of Miyanohigashi-machi, Japan

[73] Assignee: Horiba, Ltd., Kyoto, Japan

[21] Appl. No.: 09/014,236

[22] Filed: Jan. 27, 1998

[30] Foreign Application Priority Data

Jan. 31, 1997 [JP] Japan .................................. 9-033026
Jan. 31, 1997 [JP] Japan .................................. 9-033027

[51] Int. Cl.[7] ................................................. G01N 27/27
[52] U.S. Cl. ......................... 73/53.01; 324/438; 324/439
[58] Field of Search ........................... 73/53.01; 324/438, 324/439

[56] References Cited

U.S. PATENT DOCUMENTS

| | | | |
|---|---|---|---|
| 4,777,444 | 10/1988 | Beijk et al. | 324/439 |
| 4,921,582 | 5/1990 | Wang et al. | . |
| 5,103,179 | 4/1992 | Thomas et al. | 324/438 |
| 5,483,164 | 1/1996 | Moss et al. | 324/438 X |
| 5,543,717 | 8/1996 | Kordas | 324/439 X |
| 5,581,189 | 12/1996 | Brenn | . |

FOREIGN PATENT DOCUMENTS 398634  11/1990  European Pat. Off. .

OTHER PUBLICATIONS

"Problems and Solutions in pH Measurement," by S.C. Creason et al., ISA Transactions 1977, vol. 16, No. 3.

*Primary Examiner*—Daniel S. Larkin
*Attorney, Agent, or Firm*—Price, Gess & Ubell

[57] ABSTRACT

Measuring equipment, such as a portable pH meter system, can include a plurality of probes for measuring different properties of a sample with each of the probes contacting the sample simultaneously. A reference source line connected to an appropriate reference source can be connected to each probe, while a signal line connected to each probe can provide a measurement signal. A switch assembly is provided for each of the probes in order to isolate the respective probes from each other to prevent any interference when measuring the sample.

16 Claims, 6 Drawing Sheets

MEASURING EQUIPMENT FOR ISOLATING A PLURALITY OF PROBES CONTACTING A SAMPLE

BACKGROUND OF THE INVENTION

1. Field of the Invention

The present invention relates to measuring equipment for providing accurate measurements of a plurality of properties of a sample, such as dissolved oxygen, conductivity, and pH and more particularly to measuring equipment having a plurality of probes that can accurately measure a characteristic of a sample while the other probes are isolated from any interference in the measurement signals.

2. Description of Related Art

Various forms of measuring equipment for measuring at least two properties of a sample, such as at least two of dissolved oxygen, conductivity, and pH, wherein the appropriate probes are emerged in the same sample are known. Problems that are experienced in such measuring equipment are that there is an interference and an influence in the measurement by one of the probes as a result of the immersion of the other probes in the same sample. Examples of this type of measuring equipment are shown in FIGS. 4–6.

Referring to FIG. 4, one example of a configuration of conventional measuring equipment for measuring dissolved oxygen and pH is shown. The dissolved oxygen probe 31 has a pair of signal cables 32, 33 connected to the probe. One signal cable 33 has a reference potential or source connected. The other signal cable 32 is in turn connected to a current voltage converter circuit 34 whose output signal is connected to an analog to digital, A/D, converter circuit 35, which in turn is connected by a photo-coupler 36 to a processor and display unit 37. A power supply 38 is provided for driving the current-voltage converter circuit 34, the A/D converter circuit 35, and the photo-coupler 36, respectively.

A pH probe 39 is connected to a reference source by a reference line 41. In addition, a signal cable 40 is connected to an impedance converter circuit 42 whose output signal is connected to an A/D converter circuit 43. A photo-coupler circuit 44 can provide the output of the AID converter circuit 43 to the processor and display unit 37.

A power supply 45 can drive the impedance converter circuit 42, the A/D converter circuit 43, and the photo-coupler 44, respectively. In FIG. 4, the circuit I is capable of providing a measurement of the dissolved oxygen when the dissolved oxygen probe 31 is activated so that a signal is provided through the signal cable 32 to the current-voltage converter circuit 34 which is then connected to the A/D converter 35 to provide a digital output representative of the dissolved oxygen which is then connected to the processor and display unit 37 by the photo-coupler 36. The circuit II in FIG. 4 is used for measuring pH and comprises the pH probe 39, a signal cable 40, an impedance converter 42, A/D converter circuit 43, photo-coupler 44, and the processor display unit 37. The purpose of the photo-couplers 36 and 44 are to permit an isolation of the respective pH probe 39 and dissolved oxygen probe 41.

As can be appreciated, however, from reviewing the equipment configuration shown in FIG. 4, there is a duplication of circuit components since the A/D converter circuits 35 and 43, power supplies 38 and 45, and photo-couplers 36 and 44 are used, resulting not only in an increased number of component parts so that it can respectively fail, but also an increase in cost, as well as an increase in circuit area. These issues remain the same even when the dissolved oxygen probe 31 and the current voltage converter circuit 34 are replaced with a conductive probe and conductive voltage converter circuit.

FIG. 5 discloses an alternative arrangement of measuring equipment for measuring both dissolved oxygen and pH of a sample. In this configuration, switches 46 and 47 are installed, respectively, in the cable signal lines 33 and 41. When switch 47 is turned off (open condition), the pH probe 39 is isolated during the measurement of dissolved oxygen. Alternatively, switch 46 is turned off (open condition) to isolate the dissolved oxygen probe 31 when the pH measurement is being conducted. As can be seen, the current-voltage converter circuit 34 and the impedance converter circuit 42 can be both powered by the same power supply 49, while a common A/D converter circuit 48 is used, which is also powered by the same power supply 49. This design approach attempts to eliminate any interference or influence between the pH probe 39 in the dissolved oxygen measurement and any interference or influence of the dissolved oxygen probe 31 during a pH measurement. This design approach has another advantage in that only one A/D converter circuit 48 and power supply is required.

Problems and the potential for problems during the measurement cycle still exist since, when switch 46 is brought to an open state to measure pH, it takes a period of time to stabilize the potential at the dissolved oxygen probe 31 when the switch 47 is being opened and the switch 46 is being closed to measure the dissolved oxygen for the next cycle. Thus, the measurement cycle time is increased.

An alternative conductivity meter is shown in FIG. 6 and incorporates a switch 56 that is intermediately installed in the signal line cable 53 that connects the conductivity probe 51 to a reference source. Opening the switch 56 will isolate the conductivity probe 51 during a pH measurement. As can be seen, a single power supply 49 can be used to drive the conductivity-voltage converter circuit 54, the impedance converter circuit 42, and the respective A/D converter circuits 43 and 55. As a result of this design, it is possible to minimize interference and influences during the pH measurement cycle. However, when the switch 56 is electrically controlled, the switching by a semiconductor (for example, an analog switch) is used in place of a relay switch operated by electromagnetic in order to reduce the power consumption. When the switch 56 is turned on to measure conductivity, the ON resistance can exert an influence that may provide errors in the measurement results attained during the conductivity measurement. These errors have to be dealt with by a signal filtering procedure at the processor and display unit 37 and thereby increases or complicates the processing of the output signal.

The pH measuring and meter equipment field is subject to competitive pressures on the cost of equipment and accordingly there is still a demand for providing relatively simplified equipment at economical cost.

OBJECTS AND SUMMARY OF THE INVENTION

The present invention provides portable measuring equipment for measuring a plurality of properties of a sample, such as dissolved oxygen, conductivity, and pH. A dissolved oxygen probe, a conductivity probe, and a pH probe can be of a configuration for simultaneously contacting the sample and can be arranged to be connected to a hand-carried measuring monitor or meter. A first reference source is connected by a first reference source line to the pH probe, while a second reference source is connected by a second reference line to the dissolved oxygen probe. A third reference source can be connected by a third reference source line to the conductivity probe. In at least one embodiment, the same reference source can be used. A single power supply can be used to power both an A/D converter circuit, an impedance converter circuit, a current-voltage converter circuit, and a conductivity-voltage converter circuit. A microprocessor unit can process the appropriate pH signal, dissolved oxygen signal, and conductivity signal to provide the respective measurements for display.

A first switch assembly can be connected to the first reference source line, while a second switch assembly is connected to the second reference source line. Finally, a third switch assembly can be connected to the third reference source line. The switch assemblies can be appropriately controlled and automatically activated so that they can be used to isolate, respectively, the measuring probe from interference by the existence of the other probes contacting the sample.

The first switch assembly can include a first switch connected to the reference source line and a second switch connected to the signal line, with the first and second switches being opened to prevent the probe from interfering with the other probes' measurements. A second switch assembly can include a third switch connected to a reference source line which can be opened to disconnect the reference source line to prevent interference with the remaining plurality of probes. It is possible to use a switch assembly including a pair of switches that are operatively connected to an operational amplifier that is in turn connected to the reference source.

As can be appreciated, the switches can be automatically controlled by the processing circuitry, such as a microprocessor, that can appropriately address and activate each of the respective switching assemblies to accommodate the consecutive measurements of the properties of the sample. Thus, in operation, it is possible to isolate the pH probe from its reference potential when the dissolved oxygen is being measured and to in turn isolate the dissolved oxygen probe from its reference potential when the pH is being measured. The electrodes of the dissolved oxygen probe are appropriately short-circuited by the closing of its respective switching assembly. Because the electrodes in the isolated dissolved oxygen probe are short-circuited, the potential in the dissolved oxygen probe can be quickly stabilized and the dissolved oxygen measurement can be obtained quickly without any time lags in the measurement cycle. The utilization of a non-reversible type operational amplifier can be used in coordination with a set of switches, with the pair of switches being turned on or off simultaneously to assist in the measurement of conductivity or pH. As a result of this arrangement, the output impedance can be reduced to a very small amount upon turning on the switch even if the switch is formed from a semiconductor, such as an analog switch, etc., and therefore the influences caused by an ON resistance exerted in the conductivity measurement can become nearly negligible.

As can be understood, the present invention can be applied to measuring equipment for measuring a plurality of properties of a sample with separate probes contacting the sample simultaneously. The preferred embodiments are disclosed to enable the measurements of pH, dissolved oxygen, and conductivity.

BRIEF DESCRIPTION OF THE DRAWINGS

The exact nature of this invention, as well as its objects and advantages, will become readily apparent upon reference to the following detailed description when considered in conjunction with the accompanying drawings, in which like reference numerals designate like parts throughout the figures thereof, and wherein.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide an improved measuring equipment for isolating a plurality of measurement probes contacting a sample.

The present invention can be used in portable pH meters to provide an apparent simultaneous measurement of, for example, pH and an ion measurement such as a chloride ion, fluoride ion, ammonia ion, nitrate ion, calcium ion or potassium ion, or a pH measurement and a conductivity measurement, or a pH measurement and a dissolved oxygen measurement. The present invention can accommodate multiple electrode measurements, e.g., two, three, or more measurements without interference. Thus, easily handcarried meters and optional electrode accessories can provide a multifunctional pH meter.

Figure 1:
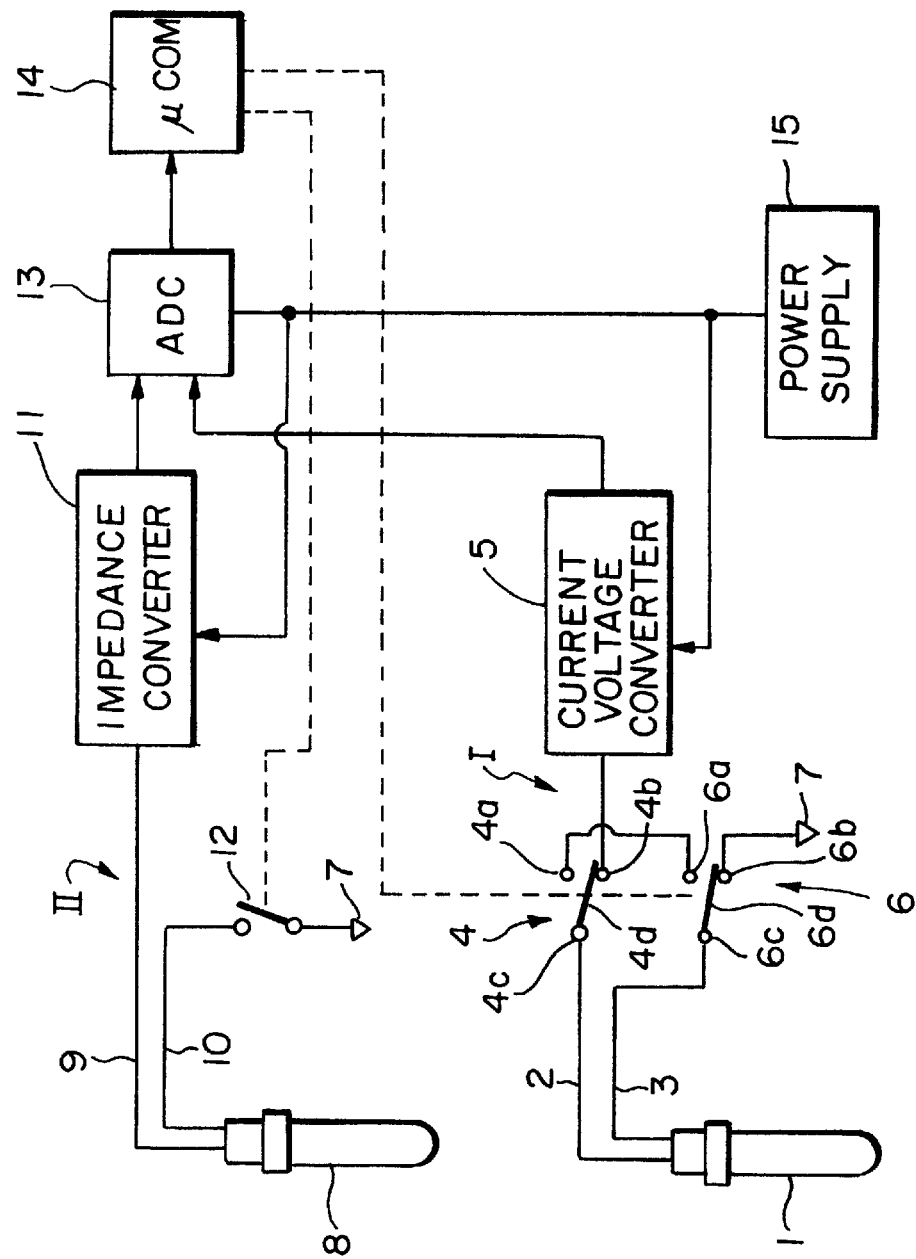
FIG. 1 is a schematic circuit showing a first embodiment of the present invention for measuring dissolved oxygen and pH.

FIG. 1 discloses a first embodiment of the present invention in a schematic form. In FIG. 1, I refers to a dissolved oxygen measuring circuit, while II refers to a pH measuring circuit. The dissolved oxygen measuring circuit I is designed to measure the current of the dissolved oxygen probe I and includes a pair of cables or connectors 2 and 3 connected respectively to a reference source 7 and a current-voltage converter circuit 5. Cable or reference source line 3 and cable or signal line 2 incorporate a first selector switch assembly 4. The first selector switch assembly 4 comprises an "a" contact terminal 4a, a "b" contact terminal 4b, a terminal 4c, and a switching member or piece 4d. The terminal 4c is connected to the signal cable 2 and the "a" contact terminal 4a is connected to the "a" contact terminal 6a of the second selector switch 6. The "b" contact terminal 4b is directly connected to the current-voltage converter circuit 5.

The reference line 3 is connected to a reference potential 7 via a second selector switch 6. More specifically, the second selector switch 6 comprises an "a" contact terminal 6a, "b" contact terminal 6b, a terminal 6c, and a switching piece 6d. The terminal 6c is connected to the signal reference source line or cable 3 and the "a" contact terminal 6a is connected to the "a" contact terminal 4a of the first selector switch 4, while the "b" contact terminal 6b is connected to the reference potential 7. This reference potential 7 is the reference potential of the entire measuring circuit I and is equivalent to the input reference potential of the A/D converter circuit 13 to be described later. The operation of the selector switches 4 and 6 are as follows:

When the section 4d of the first selector switch 4 comes into contact with the "b" contact terminal 4b to connect the dissolved oxygen probe 1 to the current-voltage converter circuit 5 via the signal cable 2, the section 6d of the second selector switch 6 is designed to come into contact with the "b" contact terminal 6b to apply the reference potential 7 to dissolved oxygen probe 1 via the signal cable 3. When the section 4d comes in contact with the "a" contact terminal 4a and the dissolved oxygen probe 1 is isolated from the current-voltage converter circuit 5, the section 6d comes in contact with the "a" contact terminal 6a and the dissolved oxygen probe 1 is isolated from the reference potential 7 and is changed over in such a manner to short circuit the pair of electrodes of the dissolved oxygen probe (not illustrated). The actuation of this changeover operation takes place on the basis of commands that can be automatically forwarded from the microprocessor and display unit 14 to be described later.

The configuration of the pH measuring circuit II includes a pH probe 8 from which two signal cables 9 and 10 are connected. Signal cable 9 is connected to the impedance converter circuit 11, while the other signal cable 10 acts as a reference source line for connection to the reference potential 7 via the switch 12. The impedance converter circuit 11 output is applied to an analog to digital converter, A/D converter circuit 13, that can be commonly utilized for both the oxygen measuring circuit I and the pH measuring circuit II. Although not shown, a selector switch can be placed on the input side of the A/D converter circuit 13, for example, an analog multiplexer that can be controlled by a microcomputer or processor in the processor and display unit 14 to thereby switch and convert the analog signal from the respective circuits I and II alternatively into a digital signal and an output to the processor and display unit 14. The microprocessor within the processor and display unit 14 has the capabilities to process the inputted signals into appropriate measurement values to display the processing results and to store them in memory. The microcomputer also can be programmed to provide various control capabilities, such as controlling the sequence of activation of the various switches for isolating those probes that are not involved in a specific measurement.

The power supply 15 can supply power to drive the current-voltage converter circuit 5, the impedance converter circuit 11, and the A/D converter circuit 13. The dissolved oxygen probe 1 and the pH probe 8 can be simultaneously immersed in the same sample (not illustrated). When the pH measurement is conducted under this condition, the switch 12 and the pH measuring circuit II is turned ON (closed) and the reference potential 7 is connected to the pH probe 8. At the same time, in the dissolved oxygen measuring circuit I, the first switch 4 and the second switch 6 are changed over and the terminals 4c, 6c and the "a" contacts 4a and 6a are connected, respectively, to thereby isolate the dissolved oxygen probe 1 from the pH measuring circuit II. At the same time, this arrangement permits the shorting of the two electrodes in the isolated dissolved oxygen probe 1. As a result of this condition, the output signal from the pH probe 8 is inputted into the A/D converter circuit 13 via the impedance converter circuit 11 and the resulting converted output is then inputted into a microprocessor in unit 14 so that the pH results of the sample can be obtained. These results can be stored and/or displayed. During this measurement cycle, the dissolved oxygen probe 1 is effectively isolated from the pH measuring circuit II, and therefore interference and influences that could occur from the contact of the dissolved oxygen probe 1 on the same sample are eliminated and a highly accurate measurement can be achieved.

When it is desired to measure dissolved oxygen, the switch 12 and the pH measuring circuit II is turned OFF (opened) to isolate the pH probe 8 from the dissolved oxygen measuring circuit I. This activation of the respective switches 12, 4, and 6 can be automatically controlled by the microprocessor and display unit 14 as shown by the dotted control lines. Thus, the first switch 4 and the second switch 6, in the dissolved oxygen measuring circuit I are respectively changed over so that the terminals 4c, 6c and "b" contacts 4b and 6b connect the dissolved oxygen probe 1 to the current-voltage converter circuit 5, while at the same time, the reference potential 7 is applied to the dissolved oxygen probe 1.

As a result of this connection, the output signal from the dissolved oxygen probe 1 is inputted to the A/D converter circuit 13 via the current-voltage converter circuit 5 and the converted output is inputted into the microprocessor and control unit 14. A measurement of the amount of dissolved oxygen in the sample is thereby obtained. Since the pH probe 8 is isolated from the dissolved oxygen measuring circuit I, any interference and influences that could affect the dissolved oxygen measurement by the presence of the pH probe 8 are thereby eliminated and a highly accurate measurement can take place. After the dissolved oxygen measurement has been achieved, it is possible to obtain the dissolved oxygen measurements at a high response rate because the dissolved oxygen probe 1 is shorted when the pH measurement is accomplished to thereby bring the dissolved oxygen electrode to a ready state.

In the above arrangement, only one A/D converter circuit 13 is required and in addition only one power supply 15 is required for driving the current-voltage converter circuit 5, the impedance converter circuit 11, and the A/D converter circuit 13. As a result, the entire circuit configuration can be simplified and the area of the circuit can be downsized.

Figure 2:
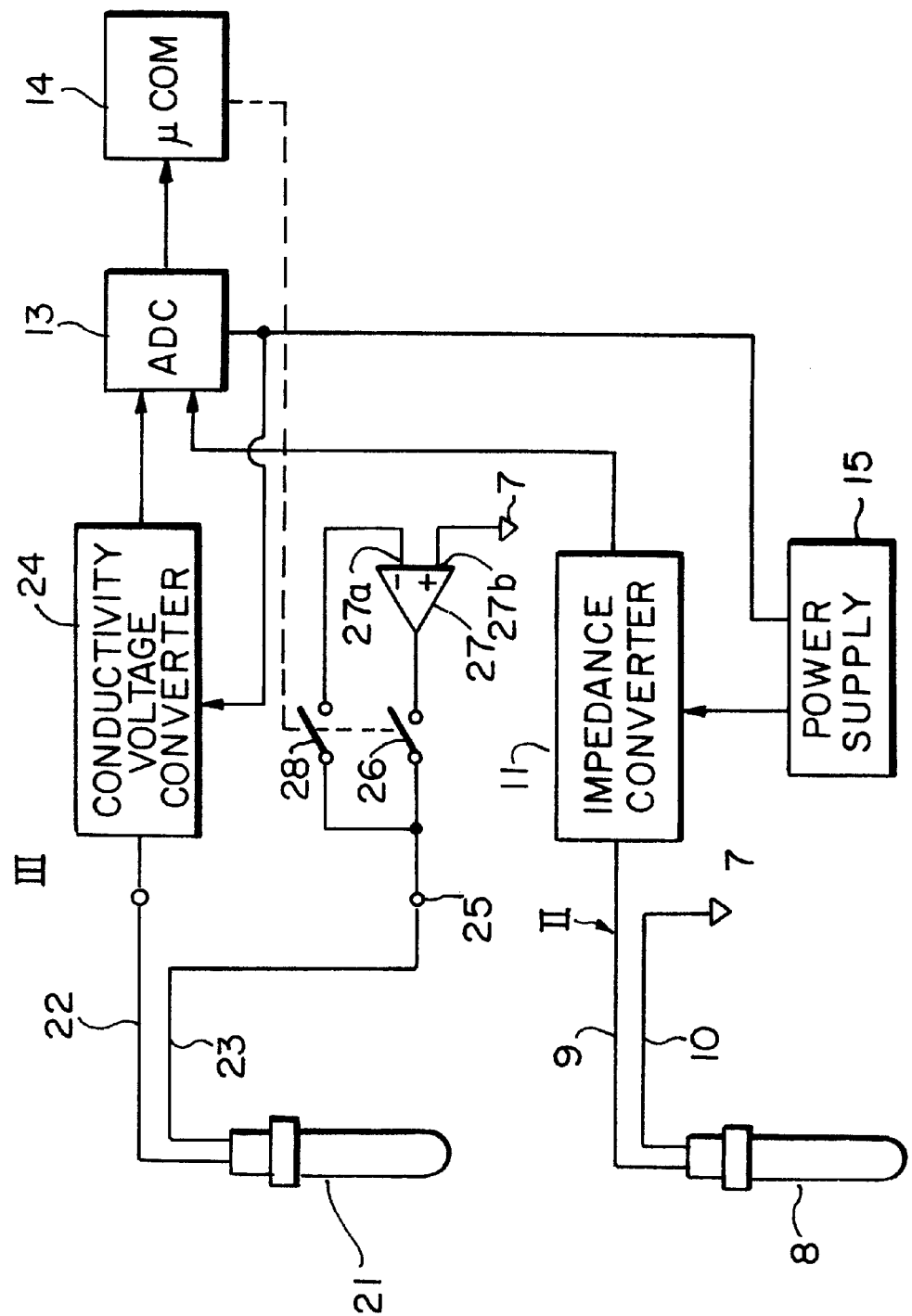
FIG. 2 is a schematic circuit of an alternative embodiment of the present invention for measuring conductivity and pH.

Referring to FIG. 2, a second embodiment of the present invention is disclosed with a pH measuring circuit II and a conductivity measuring circuit III. Since the elements set forth in FIG. 2 that are the same as the elements set forth in FIG. 1, like reference characters will be utilized and a detailed description will be omitted.

The conductivity measuring circuit III is configured to measure the current that flows when a specific voltage is applied to the conductivity electrode in the conductivity probe 21. A pair of signal cables 22 and 23 are respectively connected to the conductivity probe 21. Signal cable 22 is connected to the conductivity-voltage converter circuit 24 that can comprise, for example, a constant voltage current-voltage converter circuit for measuring the current flowing in the conductivity probe 21. Signal cable 23 is connected to the terminal 25 for providing a reference voltage dedicated to the conductivity measurement and to this terminal 25, the output side of a non-reversible type OP AMP 27 is connected via the first switch 26 which can comprise, for example, an analog switch. A second switch 28 which is turned ON or OFF simultaneously with the first switch 26, as shown by the dotted control lines, is intermediately installed between the non-reversible input terminal 27a of the non-reversible type OP AMP 27 and the terminal 25. Through the non-reversible input terminal 27b of the OP AMP 27, the pH measuring circuit II, A/D converter circuit 13, etc., similar to that of FIG. 1, can be connected to a reference potential 7 that will be common to the entire circuit. The ON/OFF switching control of the first switch 26 and a second switch 28 is again carried out on the basis of commands from the microprocessor and control unit 14. In this embodiment, the power supply 15 can commonly drive the conductivity-voltage converter circuit 24, impedance converter circuit 11, A/D converter circuit 13, etc.

When the conductivity probe 21 and the pH probe 8 are simultaneously immersed in the same sample (not illustrated), the pH can be measured when the first switch 26 and the second switch 28 are turned OFF (open condition). As a result of this switching operation, the conductivity probe 21 is isolated from the pH measuring circuit II. The output signal from the pH probe 8 is inputted into the A/D converter circuit 13 via the impedance converter circuit 11 and the converted output is inputted into the microprocessor and control unit 14 so that the pH results of the sample can be obtained. Since the conductivity probe 21 is isolated from the pH measuring circuit II, any interference and influences that could be caused by the conductivity probe 21 on the pH measurement are thereby eliminated an a highly accurate measurement can take place.

When the conductivity is being measured, switches 26, 28 are turned ON (closed condition) and the specified reference potential is applied to the conductivity probe 1. The current that flows when this specified voltage is applied is converted into voltage in the conductivity-voltage converter circuit 24, and after it is further A/D converted, it is inputted into the microprocessor and control unit 14, and the conductivity of the sample is determined. By turning the switches 26, 28 ON, it is possible to turn on the switch with the output impedance held as small as possible by bringing the voltage of the terminal 25 to a level which is the same as that of the reference potential 7 by the action of the non-reversible type OP AMP 27. Thus, the influence of the ON resistance of the switch 26 (voltage drop caused by minor current flowing the switch 28 can be ignored because the input impedance of the reverse input terminal 27a is high) can be brought to a nearly negligible level, and a highly accurate measurement can be carried out.

In the above embodiment, since only one A/D converter circuit 13 is required, as well as only one power supply 15 for driving the conductivity-voltage converter circuit 24, impedance converter circuit 11, and A/D converter circuit 13, the entire circuit configuration can be simplified, and the circuit area can be reduced.

Because the non-reversible type OP AMP 27 is intermediately installed in one signal cable 23 of the conductivity probe 21 as described above, the measurement is scarcely subject to the ON resistance when switches 26, 28 are turned ON, and consequently, it is possible to reduce the consumption power using the analog switch with comparatively large ON resistance of switches 26, 28, but relay switches with small ON resistance may also be used for switches 26, 28. The input impedance of the reverse input terminal 27a of the OP invention shall not be limited to this, but could include equipment for measuring the conductivity and dissolved oxygen.

In each of the above-mentioned embodiments for the A/D converter circuit 13, a selector switch is installed on the input side, but in place of this, a selector switch may be installed separately and an A/D converter circuit 13 without the selector switch may be used. Because in the equipment for measuring dissolved oxygen or pH according to this invention, the pH probe is designed to be isolated from the dissolved oxygen measuring circuit in measuring dissolved oxygen and the dissolved oxygen probe is designed to be isolated from the pH measuring circuit in measuring pH, and as a result, measurements are free from interference and influences caused by multiple probes, and a highly accurate dissolved oxygen measurement or pH measurement can be carried out.

In measuring pH, the dissolved oxygen probe is not only isolated from the pH measuring circuit, but also electrodes in the isolated dissolved oxygen probe are short-circuited so that the potential in the dissolved oxygen probe can be quickly stabilized and a dissolved oxygen measurement can be carried out quickly when the dissolved oxygen probe is changed over from the condition with the dissolved oxygen probe isolated from the reference potential to a dissolved oxygen measurement condition in order to carry out pH measurement.

In the equipment for measuring the conductivity or pH, the reference potential is designed to be provided to the conductivity probe via a circuit compounding the non-reversible type OP AMP with the switch at the time of conductivity measurement and the switch is turned off to isolate the conductivity probe from the pH measuring circuit at the time of pH measurement, therefore pH measurement and conductivity measurement can be carried out highly accurately.

With this invention, the circuit configuration can be simplified to connect input terminals 27a to 27b of OP AMP 27 at high resistance.

Figure 3:
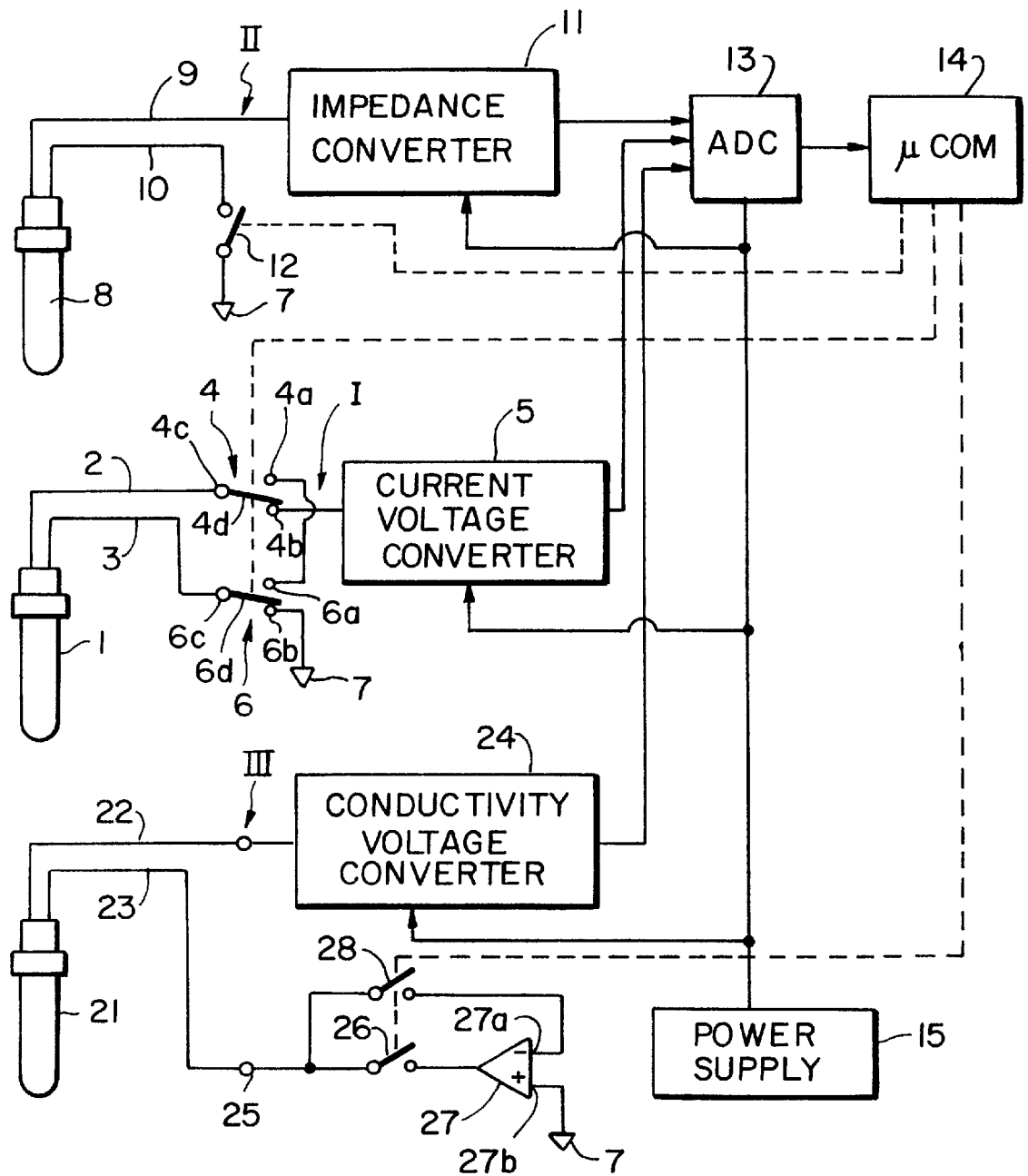
FIG. 3 is a third embodiment of the present invention for measuring dissolved oxygen, conductivity and pH according to the present invention.
Figure 4:
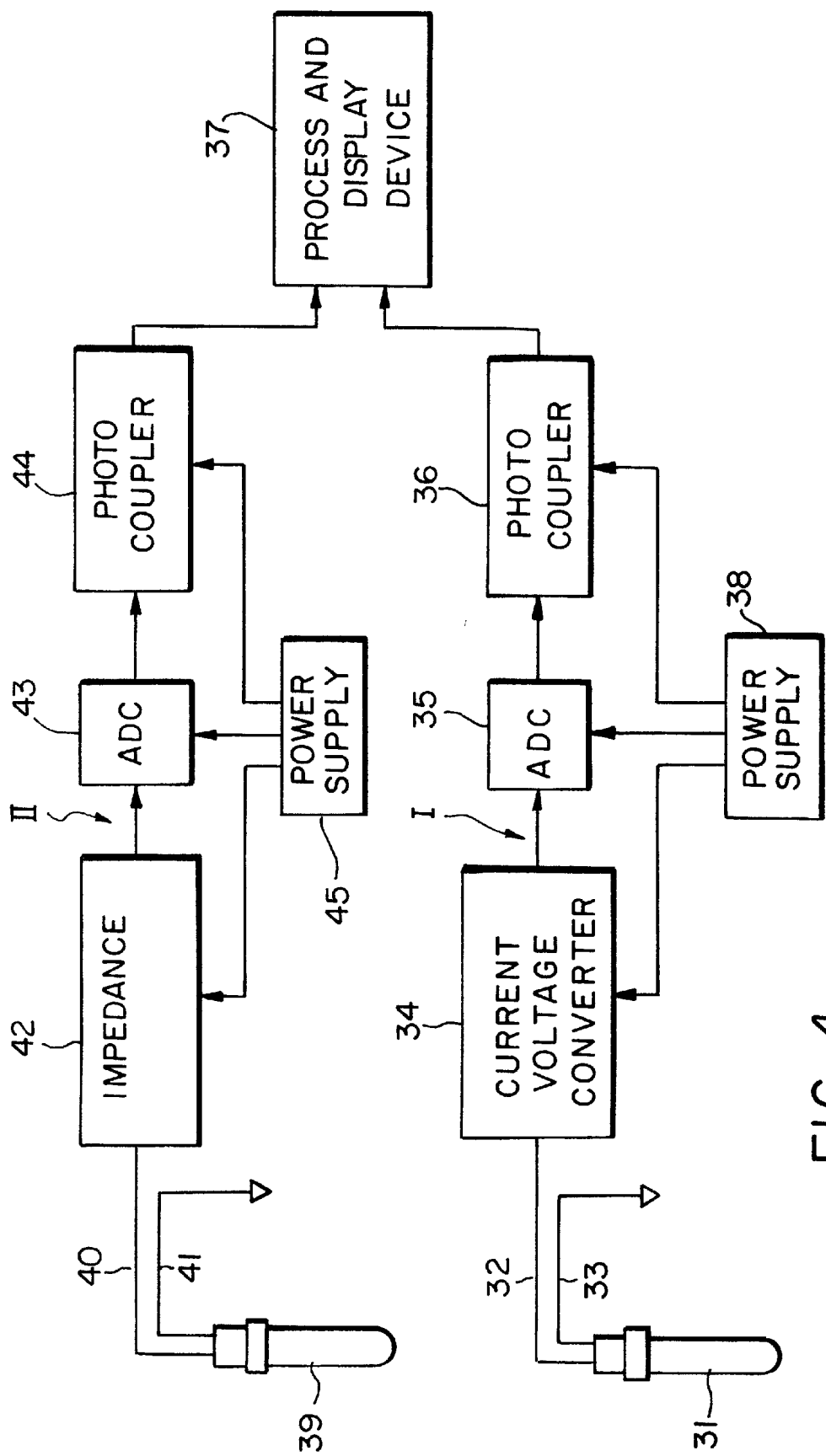
FIG. 4 is a schematic showing conventional measuring equipment for measuring dissolved oxygen or pH.
Figure 5:
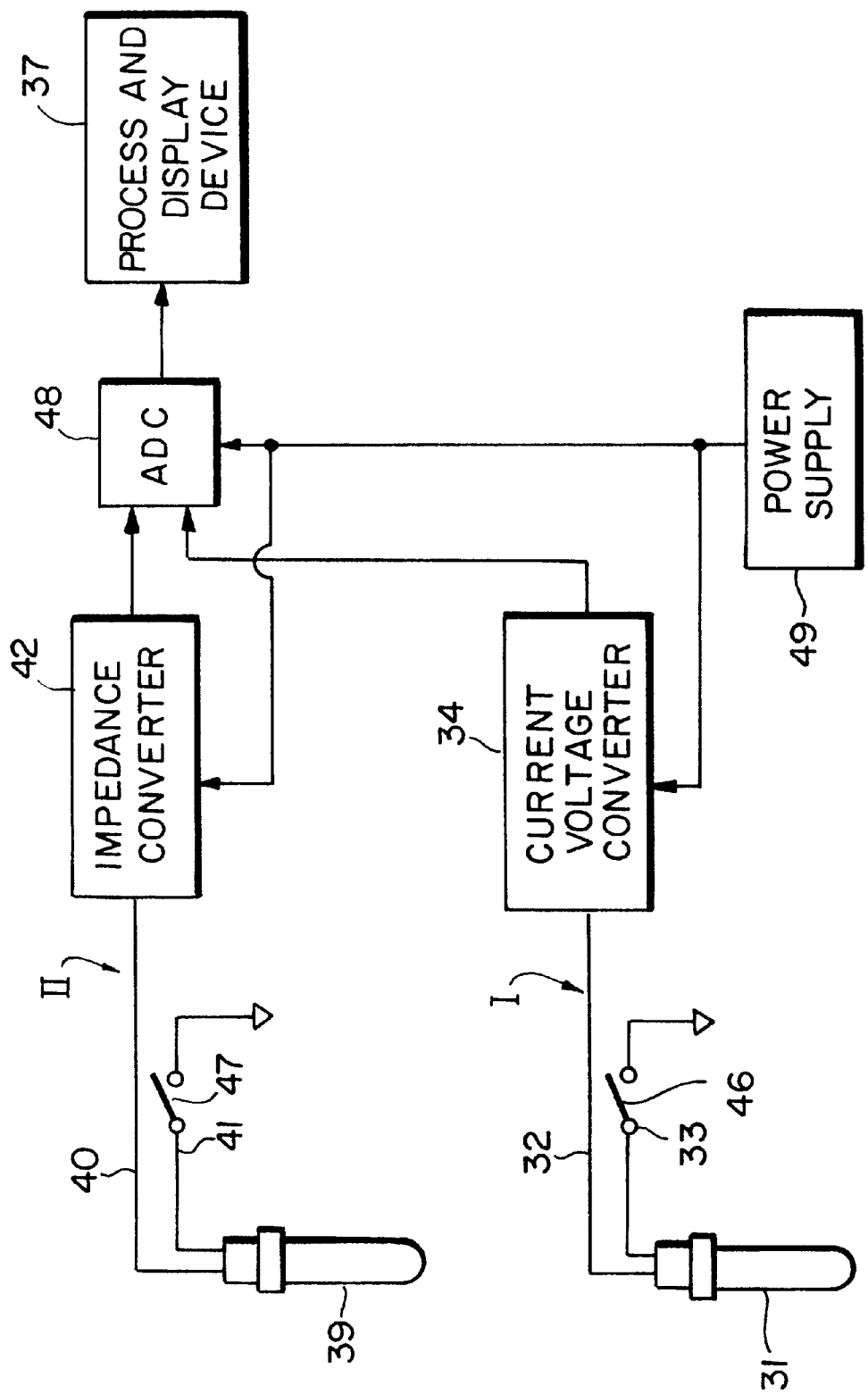
FIG. 5 is a schematic circuit for showing conventional measuring equipment for measuring dissolved oxygen or pH.
Figure 6:
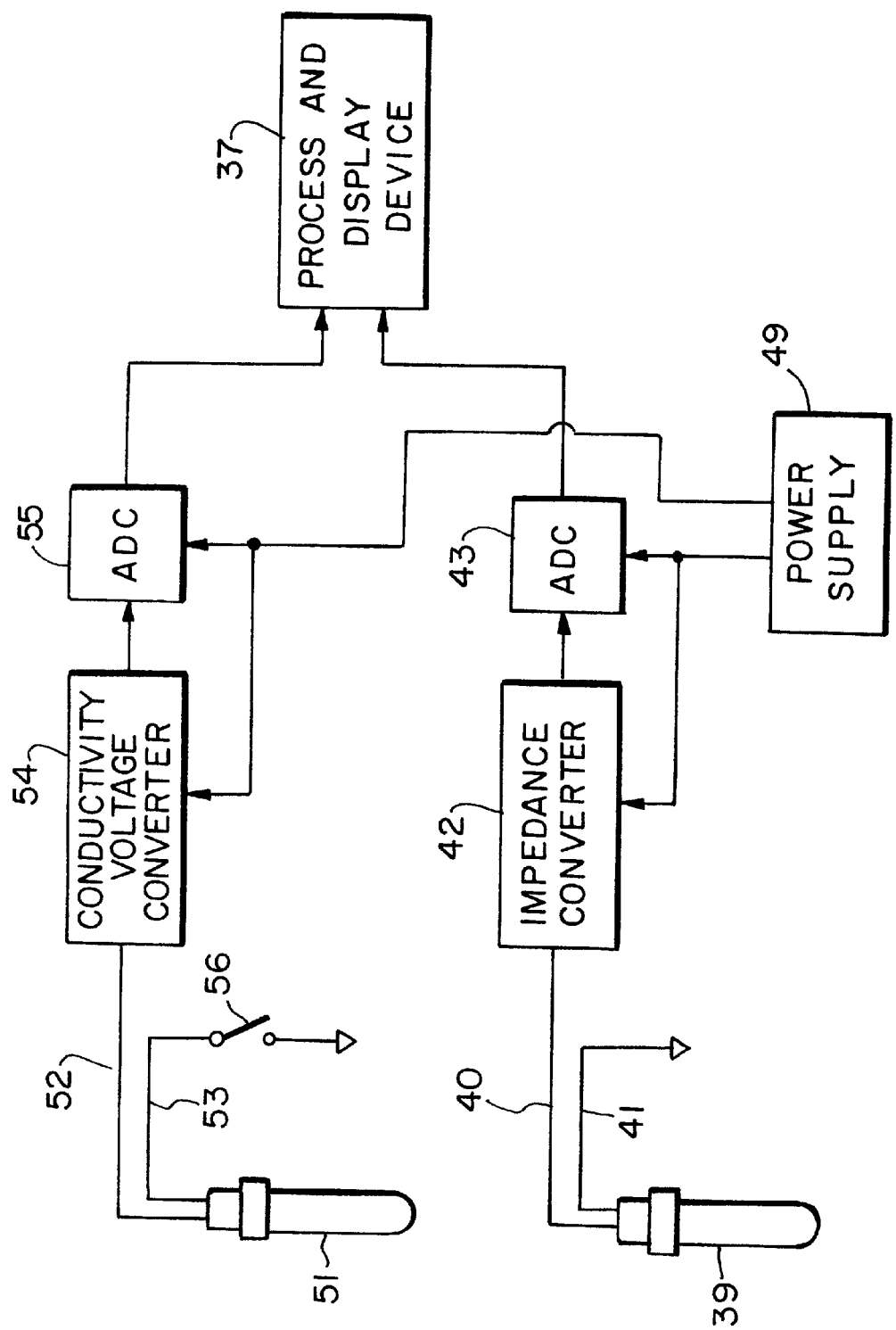
FIG. 6 is a schematic circuit for showing another conventional measuring equipment for measuring dissolved oxygen and pH.

FIG. 3 shows a third embodiment according to this invention which is capable of measuring dissolved oxygen, conductivity, and pH. In FIG. 3, drawing members carrying the same reference characters as FIG. 1 and 2 designate like or corresponding members and their description is omitted.

By connecting, as shown in FIG. 3, any interference and influences which could be caused by the conductivity probe 21 and pH probe 8 can be eliminated by isolating the conductivity probe 21 and pH probe 8 from the reference potential 7 when the dissolved oxygen is measured. Any interference and influences caused by the dissolved oxygen probe 1 and the conductivity probe 21 can be eliminated by isolating the dissolved oxygen probe 1 and the conductivity probe 21 from the reference potential 7 when the pH is measured. In addition, interference and influences caused by the dissolved oxygen probe 1 and the pH probe 8 can be eliminated by isolating the dissolved oxygen probe 1 and the pH probe 8 from the reference potential 7 when the conductivity is measured.

Because the signal cables 2, 3 of the dissolved oxygen probe 1 are short-circuited with the dissolved oxygen probe 1 isolated from the reference potential 7 in order to measure pH or conductivity, when the circuit is changed over from this condition to a state for carrying out a conductivity measurement, the potential in the dissolved oxygen probe 1 can be stabilized quickly when the signal cables 2, 3 of the dissolved oxygen probe 1 are connected to the reference potential 7 and the current-voltage converter circuit 5, respectively, and the dissolved oxygen measurement can be quickly obtained.

In addition, even if the first and the second switches 26, 28 connected to the conductivity probe 21 are formed by semiconductors such as analog switches, etc., in measuring the conductivity, influences by the ON resistance of the switches 26, 28 are scarcely exerted on the conductivity measurement, and the measurement can be easily stabilized.

In this embodiment, an example is provided in which the three probes 1, 8, and 21 are immersed in the same sample and inexpensive equipment as a whole can be obtained.

Because this invention concerns equipment for measuring two or more of dissolved oxygen, conductivity, and pH, similar effects can be achieved with equipment for measuring dissolved oxygen and conductivity and equipment for measuring dissolved oxygen, conductivity, and pH.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. Measuring equipment for measuring a plurality of properties of a sample with separate probes contacting the sample simultaneously, comprising:
   a plurality of probes;
   a reference source line connected to each probe;
   a signal line connected to each probe for providing a measurement signal; and
   a first switch assembly connected to a first reference source line and a first signal line to isolate one of said plurality of probes from generating any interference while measuring the sample.

2. The measuring equipment of claim 1 wherein the first switch assembly includes a first switch connected to the first reference source line and a second switch connected to the first signal line and the first and second switches are opened to prevent a probe of said plurality of probes connected to the first signal line and the first reference source line from interfering with said other probe's measurements.

3. The measuring equipment of claim 2 wherein another of said plurality of probes include a second switch assembly including a third switch connected to a second reference source line, the third switch is closed to connect the second reference source line when the said other probe is measuring and is open to disconnect the second reference source line to prevent interference.

4. The measuring equipment of claim 3 wherein another of said plurality of probes include a third switch assembly including a fourth switch and a fifth switch connected to an operational amplifier and the operational amplifier is connected to a third reference source line.

5. The measuring equipment of claim 4 wherein a common reference source is connected to each reference source line.

6. The measuring equipment of claim 4 wherein the first switch assembly is connected to a dissolved oxygen probe, the second switch assembly is connected to a pH probe and the third switch assembly is connected to a conductivity probe.

7. The measuring equipment of claim 6 wherein the measuring equipment is of a dimension to be hand-carried by the user.

8. The measuring equipment of claim 1 wherein the first switch assembly includes a pair of switches and an operational amplifier connected to the first reference source line.

9. The measuring equipment of claim 8 wherein another of said plurality of probes include a second switch assembly including a third switch connected to a second reference source line, the third switch is closed to connect the second reference source line when the said other probe is measuring and is open to disconnect the second reference source line to prevent interference with said remaining plurality of probes.

10. The measuring equipment of claim 9 wherein said plurality of probes includes a dissolved oxygen probe.

11. The measuring equipment of claim 9 wherein said plurality of probes includes a pH probe and a conductivity probe.

12. Measuring equipment for measuring pH and dissolved oxygen, comprising:
    a pH probe for providing a pH measurement signal;
    a dissolved oxygen probe for providing a measurement dissolved oxygen signal, the pH probe and dissolved oxygen probe have a configuration for simultaneously contacting a sample;
    a first reference source;
    a first reference source line connecting the pH probe to the first reference source;
    a second reference source;
    a second reference source line connecting the dissolved oxygen probe to the second reference source;
    means for processing the pH signal and dissolved oxygen signal to provide respectively a measurement of pH and dissolved oxygen;
    a first switch assembly connected to the first reference source line;
    a second switch assembly connected to the second reference source line; and
    means for controlling the first and second switch assemblies to isolate the pH probe and the dissolved oxygen probe during their consecutive measurements to prevent interference in providing their measurement signals.

13. Apparatus for measuring dissolved oxygen and pH in a sample, comprising:
    a dissolved oxygen probe (1) and a pH probe (8) for immersion in the same sample;
    means for isolating the dissolved oxygen probe from a reference potential (7) during measurement with the pH probe, characterized by
    means (12) for isolating the pH probe from the reference potential during measurement with the dissolved oxygen probe; and
    means (4, 6) for short-circuiting electrodes of the dissolved oxygen probe during measurement with the pH probe.

14. The apparatus as in claim 13, comprising additionally:
    a conductivity probe (21) for measuring the conductivity of the same sample;
    means (22) for connecting the conductivity probe to a conductivity-voltage converter (24);
    means (23) for connecting the conductivity probe to a reference potential (7), and
    switching means (25, 26, 27, 28) for isolating the conductivity probe from the reference potential during measurement with the pH probe, whereby the switching means is constituted by a non-inverting type operational amplifier (27) and first and second switches (26, 28), the reference potential is connected to a non-inverting input of the operational amplifier (27b), the connecting means (23) is connected to the output of the operational amplifier via the first switch (26) and to an inverting input (27*b*) of the operational amplifier via the second switch (28), and the two switches (26, 28) open and close simultaneously.

15. An apparatus for measuring conductivity and pH of a sample, comprising a conductivity probe (21) and a pH probe (8) for immersion in the same sample characterized by:

means (22) for connecting the conductivity probe to a conductivity-voltage converter (24);

means (23) for connecting the conductivity probe to a reference potential (7), and switching means (25,26,27,28) for isolating the conductivity probe from the reference potential during measurement with the pH probe, whereby the switching means is constituted by a non-inverting type operational amplifier (27) and first and second switches (26,28), the reference potential is connected to a non-inverting input of the operational amplifier (27*b*), the connecting means (23) is connected to the output of the operational amplifier via the first switch (26) and to an inverting input (27*b*) of the operational amplifier via the second switch (28), and the two switches (26,28) open and close simultaneously.

16. An apparatus for measuring a conductivity of and a dissolved oxygen in a sample, comprising a conductivity probe (21) and a dissolved oxygen probe (1) for immersion in the same sample characterized by:

means (23) for connecting the conductivity probe to a conductivity-voltage converter (24);

means (23) for connecting the conductivity probe to a reference potential (7);

a first switching means (25,26,27,28) for isolating the conductivity probe from the reference potential during measurement with the dissolved oxygen probe, whereby the first switching means is constituted by a non-inverting type operational amplifier (27) and first and second switches (26,28), and the reference potential is connected to a non-inverting input of the operational amplifier (27*b*), the connecting means (23) is connected to the output of the operational amplifier via the first switch (26) and to an inverting input (27*b*) of the operational amplifier via the second switch (28), and the two switches (26,28) open and close simultaneously, and a second switching means (4,6) for isolating the dissolved oxygen probe and short-circuiting its electrodes during measurement with the conductivity probe.

\* \* \* \* \*